(12) United States Patent
Kruecker et al.

(10) Patent No.: US 10,113,889 B2
(45) Date of Patent: Oct. 30, 2018

(54) QUALITY ASSURANCE SYSTEM AND METHOD FOR NAVIGATION-ASSISTED PROCEDURES

(71) Applicant: KONINKLIJKE PHILIPS N.V., Eindhoven (NL)

(72) Inventors: Jochen Kruecker, Washington, DC (US); Shyam Bharat, Cortlandt Manor, NY (US); Cynthia Ming-Fu Kung, New York, NY (US)

(73) Assignee: Koninklijke Philips N.V., Eindhoven (NL)

( * ) Notice: Subject to any disclaimer, the term of this patent is extended or adjusted under 35 U.S.C. 154(b) by 711 days.

(21) Appl. No.: 14/388,325

(22) PCT Filed: Mar. 26, 2013

(86) PCT No.: PCT/IB2013/052387
§ 371 (c)(1),
(2) Date: Sep. 26, 2014

(87) PCT Pub. No.: WO2013/144832
PCT Pub. Date: Oct. 3, 2013

(65) Prior Publication Data
US 2015/0051861 A1    Feb. 19, 2015

Related U.S. Application Data

(60) Provisional application No. 61/617,082, filed on Mar. 29, 2012.

(51) Int. Cl.
*G01D 18/00* (2006.01)
*G01N 29/04* (2006.01)
(Continued)

(52) U.S. Cl.
CPC ............. *G01D 18/00* (2013.01); *A61B 5/061* (2013.01); *A61B 17/3403* (2013.01); *A61B 34/20* (2016.02); *A61N 5/1007* (2013.01); *G01B 7/003* (2013.01); *G01H 17/00* (2013.01); *G01N 29/04* (2013.01); *A61B 2017/00725* (2013.01); *A61B 2017/3411* (2013.01); *A61N 2005/1012* (2013.01)

(58) Field of Classification Search
None
See application file for complete search history.

(56) References Cited

U.S. PATENT DOCUMENTS 5,787,886 A    8/1998  Kelly et al.
5,899,860 A    5/1999  Pfeiffer et al.
(Continued)

FOREIGN PATENT DOCUMENTS

CN    1469720 A     1/2004
CN    202060796 U   12/2011

OTHER PUBLICATIONS

Kojima, Haruna et al., "New method for obtaining position and time structure of source in HDR remote afterloading brachyther", Journal of Applied Clinical Medical Physics, vol. 10, No. 3, 2009, p. 86-95.

*Primary Examiner* — Ahn T. N. Vo (57) ABSTRACT

A calibration system includes a channel block (102) having a plurality of channels (104) formed therein. The channels are configured to correspond to locations where treatment devices are inserted for treatment of a patient. The channels are dimensioned to restrict motion of the treatment devices. A tracking system (128) is configured to monitor a position of a treatment device (108) inserted in one or more of the channels. The tracking system is configured to generate tracking data for the at least one treatment device for comparison with an expected position for the treatment device.

20 Claims, 8 Drawing Sheets

(51) Int. Cl.
    *G01B 7/00*           (2006.01)
    *G01H 17/00*         (2006.01)
    *A61B 5/06*           (2006.01)
    *A61N 5/10*           (2006.01)
    *A61B 17/34*         (2006.01)
    *A61B 34/20*         (2016.01)
    *A61B 17/00*         (2006.01)

(56) References Cited

U.S. PATENT DOCUMENTS

| | | | | |
|---|---|---|---|---|
| 6,129,670 | A * | 10/2000 | Burdette | A61B 34/20 |
| | | | | 600/427 |
| 6,139,544 | A * | 10/2000 | Mikus | A61B 18/02 |
| | | | | 600/439 |
| 6,311,084 | B1 * | 10/2001 | Cormack | A61N 5/1007 |
| | | | | 600/411 |
| 8,141,558 | B2 | 3/2012 | Govari | |
| 8,721,514 | B2 | 5/2014 | Shechter et al. | |
| 9,101,395 | B2 | 8/2015 | Gutierrez et al. | |
| 2007/0043291 | A1 * | 2/2007 | Fidel | A61B 8/12 |
| | | | | 600/439 |
| 2007/0078327 | A1 | 4/2007 | Kindlein | |
| 2008/0216239 | A1 | 9/2008 | Luginbuhl et al. | |
| 2009/0118724 | A1 * | 5/2009 | Zvuloni | A61N 7/02 |
| | | | | 606/27 |
| 2009/0198094 | A1 | 8/2009 | Fenster et al. | |
| 2010/0268072 | A1 | 10/2010 | Hall et al. | |
| 2010/0324541 | A1 | 12/2010 | Whitman | |
| 2011/0166410 | A1 | 7/2011 | Gutierrez et al. | |
| 2011/0184684 | A1 | 7/2011 | Li et al. | |
| 2015/0051861 | A1 | 2/2015 | Kruecker et al. | |

* cited by examiner

QUALITY ASSURANCE SYSTEM AND METHOD FOR NAVIGATION-ASSISTED PROCEDURES

This application is a national stage application under 35 U.S.C. § 371 of International Application No. PCT/IB2013/052387 filed on Mar. 26, 2013 and published in the English language on Oct. 3, 2013 as International Publication No. WO 2013/144832 A1, which claims priority to U.S. Application No. 61/617,082 filed on Mar. 29, 2012, the entire disclosures of which are incorporated herein by reference.

This disclosure relates to medical instruments and more particularly to systems and methods for accuracy checking and correcting for navigation-assisted therapy.

Brachytherapy (including low-dose rate (LDR) and high-dose rate (HDR) brachytherapy) is one of the most common treatment modalities for prostate cancer. In LDR brachytherapy, radioactive seeds are permanently implanted into the prostate using trans-perineal needle access to the prostate through a grid template with the aid of transrectal ultrasound (TRUS) image guidance. In HDR brachytherapy, catheters are temporarily implanted into the prostate trans-perineally with TRUS guidance, followed by computer-controlled temporary insertion of a high-dose rate radioactive source into the catheters.

As with other medical equipment used for therapeutic purposes, the brachytherapy equipment needs to be regularly tested in quality assurance (QA) procedures and possibly re-calibrated in quality control (QC) procedures on-site in hospitals or other locations by medical physicists.

Both methods (LDR and HDR) have proven very effective in curing prostate cancer, but both suffer from variable and potentially severe side effects, variable clinical outcomes depending on the experience of the operator, and cumbersome clinical workflows.

In accordance with the present principles, to address these limitations, the use of navigation based systems such as electromagnetic (EM) tracking is employed. EM tracking allows more accurate deposition of LDR seeds and HDR catheters, mapping and monitoring of LDR seeds and HDR catheters, and thus enables an adaptive workflow in which plan creation, execution and iterative plan updating are tightly integrated to ensure optimal delivery of the therapeutic dose.

The present principles find application in any clinical navigation-assisted therapy. In particular, a brachytherapy solution (e.g., LDR and HDR) for prostate or other target organs will be described as examples. Other navigation solutions, using EM or other tracking technologies are also contemplated.

A calibration system in accordance with the present principles includes a channel block having a plurality of channels formed therein. The channels are configured to correspond to locations where treatment devices are inserted for treatment of a patient. The channels are dimensioned to restrict motion of the treatment devices. A tracking system is configured to monitor a position of a treatment device inserted in one or more of the channels. The tracking system is configured to generate tracking data for the at least one treatment device for comparison with an expected position for the treatment device.

Another calibration system includes a channel block having a plurality of channels formed therein. The plurality of channels is configured to correspond to locations where treatment devices are inserted for treatment of a patient. The channels are dimensioned to restrict motion of the treatment devices. A tracking system is configured to monitor a position of at least one treatment device inserted in at least one of the channels of the plurality of channels. The tracking system is also configured to generate tracking data for the at least one treatment device. A workstation includes a processor and memory. The memory stores a program module configured to collect the tracking data for comparison with expected position data for the at least one treatment device.

A method for system calibration includes the steps of providing a channel block having a plurality of channels formed therein, the plurality of channels being configured to correspond to locations where treatment devices are inserted for treatment of a patient, the channels being dimensioned to restrict motion of the treatment devices; tracking a position of at least one treatment device inserted in at least one of the channels of the plurality of channels using a tracking system configured to generate tracking data for the at least one treatment device; and comparing the tracking data with expected position data for the at least one treatment device.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

In accordance with the present principles, a quality assurance system and workflow are presented that may be employed to ascertain spatial accuracy and to correct for any inaccuracies in navigation-assisted brachytherapy, and in particular prostate brachytherapy. Prostate brachytherapy is one of the most common treatment modalities for prostate cancers, but it suffers from limited image guidance, which can lead to side effects in patients and can lead to user-dependent clinical outcomes. Navigation-assisted brachytherapy improves the accuracy and clinical benefit of brachytherapy. However, for this approach to be clinically acceptable, the functionality and accuracy of the navigation equipment needs to be verifiable in regular intervals in easy-to-perform QA (quality assurance) experiments.

Electromagnetic tracking (EM tracking) is an example of one navigational approach, although other navigational approaches are contemplated. Regardless of the navigational approach employed, associated equipment, workflows and technologies are introduced into the procedure. For most medical equipment, there needs to be a QA procedure in place for these new components and workflows. Currently, no hardware or software is known that permits carrying out QA and QC procedures for EM tracking in brachytherapy in an efficient, reproducible and accurate manner. The present disclosure describes systems and methods to carry out quality assurance methods to efficiently and accurately maintain a level of confidence in the integrity of equipment for clinical use in brachytherapy or other procedures.

In one embodiment, a channel block is provided that physically constrains spatially tracked brachytherapy needle motion to perfectly straight paths perpendicular to a brachytherapy grid. This forces the needle to travel inside one of a multitude of "channels" (one channel for each grid hole). A system is provided that allows acquisition and processing of tracking information from tracked needles that are inserted in the channels of the needle channel block. A software program directs the operator to follow a QA workflow which includes inserting one or several spatially tracked needles into one or several channels in the needle channel block. The program records position tracking data from the inserted needles and compares the recorded data with expected path data. A warning is provided if the recorded data does not meet requirements. If needed, the program re-calibrates the tracking system based on the already recorded or additionally requested tracking data.

In one embodiment, a workflow is employed that comprises, e.g., setting up a clinically used grid, a stepper, navigation and ultrasound equipment, and the needle channel block; and inserting tracked needle(s) in several grid holes and channel tracks until sufficient data for assertion of system accuracy is collected. Optionally, the tracking system is re-calibrated if the recorded tracking data does not meet the requirements. Also, optionally, the above steps are repeated after re-calibration to ensure that the re-calibration was successful.

It should be understood that the present invention will be described in terms of medical instruments; however, the teachings of the present invention are much broader and are applicable to other instruments where navigation is needed for precise location or placement. In some embodiments, the present principles are employed in tracking or analyzing complex biological or mechanical systems. In particular, the present principles are applicable to internal tracking procedures of biological systems, radiation sources, medications, etc. and can be related to procedures in all areas of the body such as the lungs, gastro-intestinal tract, prostate, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software, in association with the appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Figure 1:
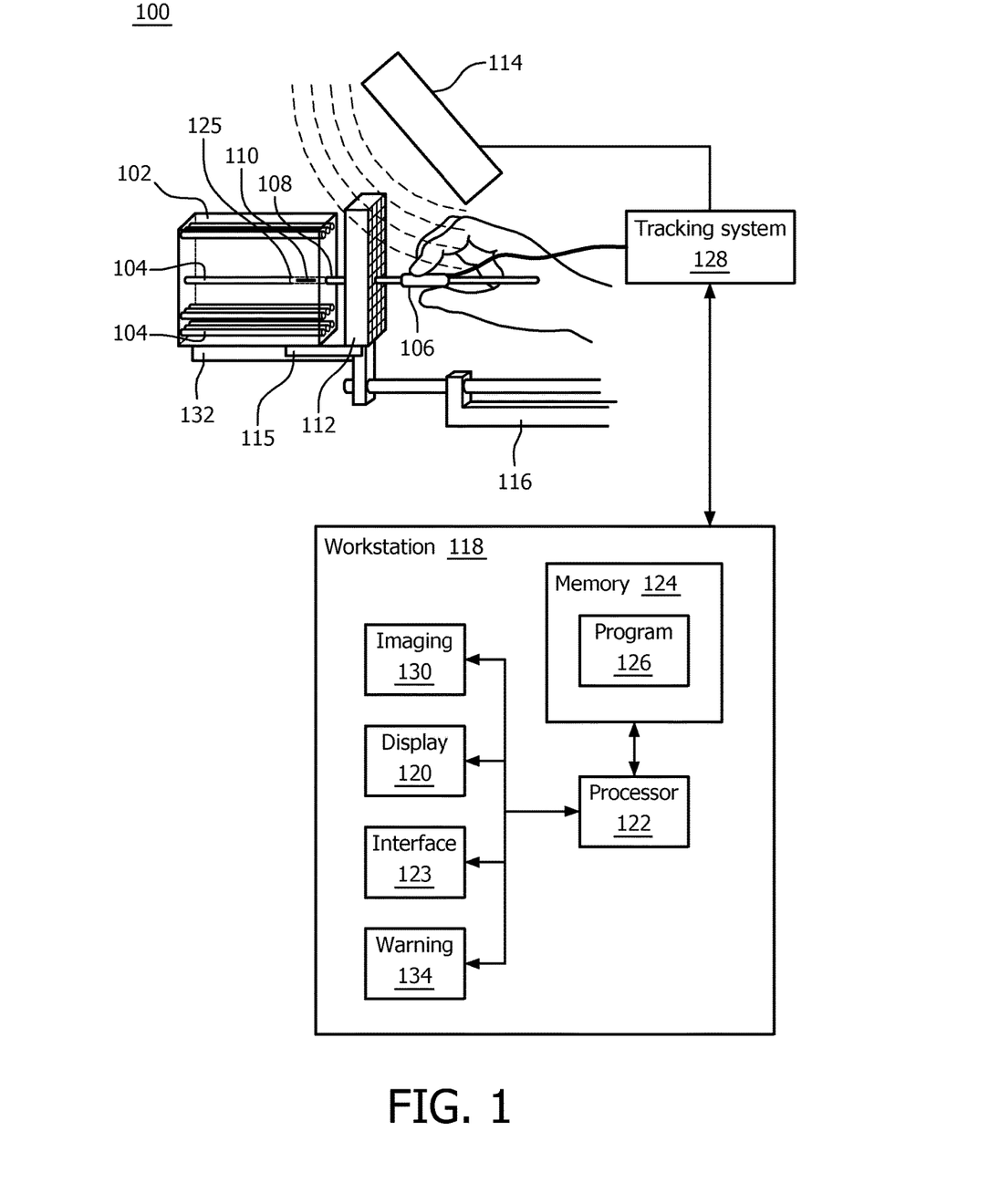
FIG. 1 is a block/flow diagram showing an illustrative calibration system for calibrating positional accuracy for a medical procedure (e.g., brachytherapy) in accordance with the present principles.

Referring now to the drawings in which like numerals represent the same or similar elements and initially to FIG. 1, a system 100 for calibrating and correcting spatial accuracy in surgical devices is illustratively shown. System 100 illustratively depicts and employs an EM tracking navigation system 128 for tracking the placement of radioactive seeds or catheters in brachytherapy. EM tracking or other navigation approaches need to have at least their positional accuracy checked to ensure the proper placement of seeds during a procedure. Other tracking technologies that may be employed include, e.g., optical, fiber-optical, acoustical or mechanical tracking technologies. In addition, the present principles may be applicable and/or customized for procedures other than prostate brachytherapy, e.g., brachytherapy of the liver, breast, etc., non-brachytherapy prostate applications such as prostate biopsy, prostate ablations, or other therapy procedures for the prostate or other organs. Other applications are also contemplated and may include QA or elated equipment such as QA of an ultrasonic probe or other imaging device.

The system 100 includes a channel block 102, which may include a volume having a plurality of channels 104 formed therein. The channel block 102 may include a sterilizable material, but any suitable material may be employed. The material should be stable under temperature changes and be capable of positionally refined placement of the channels 104 therein. Since EM tracking is employed in this embodiment, the block 102 should not include magnetic or magnetizable materials, although other navigational methods may permit magnetic or magnetizable materials. In accordance with one useful embodiment, the block 102 includes a stable polymer material, such as polyvinyl chloride (PVC), polycarbonate or the like. In addition, it may be preferred that the block be transparent so that objects placed in the channels 104 are also visible.

The channels 104 of the channel block 102 are employed to physically constrain motion of spatially tracked devices 106, e.g., therapy devices 108 (such as e.g., brachytherapy needles) having a tracking sensor 110 mounted thereon or therein. The sensor 110 may include an EM sensor although other sensors may be employed. In the example shown, the channels 104 include straight paths perpendicular to a brachytherapy grid template or grid 112. The grid template or grid 112 is employed to locate a position as a starting point for introducing needles or other objects into a patient, and this is simulated by forcing the needle 108 to travel inside one of the channels 104. It is preferable that only one channel 104 exists for each grid hole in the grid 112. The channel block 102 is employed in conjunction with other parts of system 100 to acquire and process tracking data obtained from tracked needles 108 inserted into the channel block 102.

The tracking sensors 110 are responsive to a magnetic field generator 114. The channel block 102 is mounted on a mounting device 115 immediately behind (or instead of) the grid template 108 on a stepper 116 and serves to guide the electromagnetically tracked needle 108 on a straight path in the channel 104. The channel block 102 is mounted within the field of view of the electromagnetic field generator (FG) 114, and tracking information from the sensor 110 inside the needle 108 (e.g., inside the needle tip) is acquired in a tracking system 128 and then further processed in a processing workstation 118 with a display unit 120.

The tracking system 128 may include, e.g., the Aurora™ system (by Northern Digital Inc., Waterloo, ON, Canada). The field generator 114 and the tracking system 128 (control unit), are positioned such that a tracked needle tip 125 is in the field of view of the field generator 114 for all positions inside the channel block 102 and at the surface of the template grid 112 at positions that are to be sampled. Tracking data is transferred from the tracking system 128 to the workstation 118 in real-time. On the workstation 118, tracking data is stored, processed and visualized to compare the actually obtained tracking data with expected data according to the specifications of the system 100. The workstation 118 runs software and algorithms—further detailed below—to facilitate quality assurance (QA) and quality control (QC) of the navigation functionality. In particular, the workstation 118 indicates whether the tracking accuracy meets requirements, and provides mechanisms and algorithms to correct for inaccuracies such that the corrected tracking data will meet accuracy requirements.

The workstation 118 may include a console from which a procedure is supervised and/or managed. Workstation 118 preferably includes one or more processors 122 and memory 124 for storing programs and applications. An imaging system 130 may be provided and employed during a procedure. Imaging system 130 collects imaging data and renders the data on display 120. In one embodiment, the imaging system 130 may be employed to generate data on a position of a needle 108. In one embodiment, the imaging system 130 includes an ultrasonic imaging system. An ultrasonic probe 132 may be connected to the stepper 116 for use during a procedure.

Memory 124 may store programs for controlling the stepper 116 to move a position of the grid 112. The memory 124 may include a program module 126 that directs a quality assurance (QA) work flow in accordance with the present principles. Module 126 is configured to direct an operator to follow a QA workflow. Module 126 may permit initialization of the grid 112, stepper 116, navigation and ultrasound equipment (imaging system 130) with the needle channel block 102. To check the accuracy of needle placement, the tracked needle(s) 108 are inserted into one or more grid holes to enter the channel tracks 104. This includes inserting one or several spatially tracked needles 108 into one or several channels 104 in the channel block 102 until sufficient data for assertion of system accuracy is collected. The module 126 records position tracking data from the tracking system 128, which is gathered from the inserted needles 108 with the sensors 110. The module 126 compares the recorded data with expected path data. Expected path data may be derived from expectations generated for a particular grid position, stepper setting, arbitrarily set data, data from a surgical plan, etc. In one example, the pattern of placement of the needle 108 into the channels 104 is known, and the distances of the channels 104 relative to each other is known. Therefore, the needle 108 position pattern can be checked against the known distance data to evaluate accuracy. Other tests or checks are also contemplated.

If the module 126 determines that the recorded data does not meet requirements, a warning device 134 generates an output warning (e.g., a display on the display 120 or an audible alarm or other output may be generated). Module 126 may provide suggestions for correcting out of specification recorded data. For example, if needed, the tracking system 128 based on the already recorded or additionally requested tracking data may be re-calibrated to see if the issue is addressed. The optional re-calibrating of the tracking system 128 is performed if the recorded tracking data does not meet requirements. In addition, the entire test or portions of the test may be repeated after re-calibration to ensure that the re-calibration was successful. Suggestions may include moving the grid 112 over a determined distance in a particular direction to provide improved accuracy. Other corrective actions are also contemplated.

Module 126 is configured to provide workflow instructions for a user through an interface 123 and/or display 120 for quality assurance reporting, reviewing process steps, tracking data and archiving data. The system 100 may include a remote connection for remote data transfer to an agent outside the setting where the system 100 is being employed (e.g., the vendor or service contractor of the system 100).

While the system 100 and use of the channel block 102 serves to guide a tracked needle 108 on paths within the field of view of the tracking system 128, the use of the channel block 102 is illustratively described in combination with electromagnetic (EM) tracking and prostate brachytherapy QA procedures. However, use of other tracking technologies and applications for other brachytherapy and non-brachytherapy procedures are envisioned as well.

Figure 2:
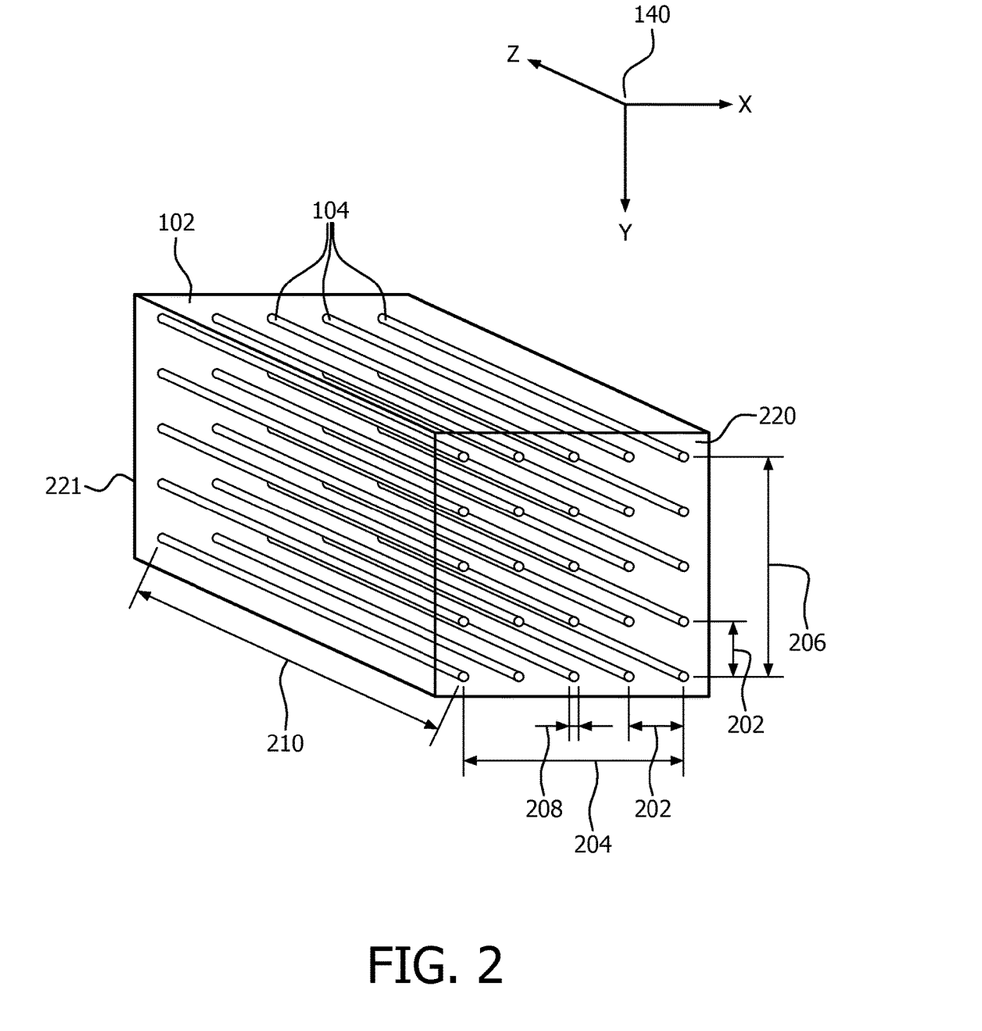
FIG. 2 is a perspective view showing a transparent channel block in use as part of a quality assurance (QA) system in accordance with one illustrative embodiment.

Referring to FIG. 2, a more detailed view of an embodiment of the channel block 102 is illustratively shown having uniformly spaced channels 104. The channel block 102 may be formed from materials that do not disturb an EM tracking field or otherwise interfere with the EM tracking technology. In particular, the channel block 102 is made primarily of non-metallic materials such as PVC or other plastic materials. The channel block 102 may include a block of solid material, e.g., rectilinear in shape (or other shape), in which channels 104 with known geometry are formed. Alternately, the channel block 102 may formed from solid segments or portions and may be reconfigurable and assembled in accordance with a given application or test.

Nomenclature of the coordinate system of the channel block 102 is illustratively set as follows. The channel block 102 has a front face 220 which is oriented to and and parallel with the grid template 112 (FIG. 1), and a back face 221 which is opposite the front face and oriented away from the grid template 112. A coordinate system 140 will be employed where the direction from front face 220 to back face 221 is designated as the +z direction; the plane perpendicular to the z-direction and thus parallel to the grid template 112 is the xy-plane. The x-direction corresponds to the rows of the grid template (left to right))), and the y-direction shall correspond to the columns of the grid (top to bottom).

In one embodiment, the channel block 102 includes parallel channels 104, each channel 104 corresponding to one hole in a grid template 112, such that with proper mounting of the channel block 102 relative to the grid 112, a needle or other device (108) can be inserted through any of the holes in the grid template 112 and into the corresponding channel 104 of the channel block 102. All the positions on grid 112 need not have a corresponding channel 104. A spacing 202 between channels 104 may be set to a given value or multiple values. In one embodiment, the channel spacing 202 is 2.5 mm (or multiples thereof, in particular: 5 mm or 10 mm) in the x and y directions. In this embodiment, a total extent 204 is shown in the x direction, and a total extent 206 is shown in the y direction of the block 102. The x and y spacings may have different values. The extents 204 and 206 are between about 5 cm and about 8 cm in this example. This spacing and size makes the needle channel geometry compatible with most grid templates currently on the market, which typically consist of rows and columns of holes with uniform hole spacings of 2.5 or 5 mm, covering a total width and height of about 5 to 7 cm. It should be understood that other spacings and arrangements are contemplated.

A diameter 208 of the channels 104 is preferably constant and identical for all channels. However, this may vary for different tools and applications. In one embodiment, the diameter may be customized for individual brachytherapy needles or catheter sizes to provide a snug fit for commonly used brachytherapy devices (e.g., 17 G (gauge) or 18 G for LDR brachytherapy needles, or 6 F (French) for HDR catheters). The channel block 102 may feature channels 104 with a multitude of diameters to be compatible with a multitude of differently sized needles. The appropriate channel size in the channel block 102 may be selected for use by an appropriate mounting of the channel block 102 relative to the grid 112, such that needles inserted through the grid 112 enter channels 104 of a correct diameter size only. This can be achieved by, e.g., alternating channels with two different diameters ("smaller" and "larger") and providing for two mounting options of the channel block 102 relative to the grid 112 such that either the smaller or the larger set of channels is aligned with the grid holes.

A total extent 210 of the channels 104 along the z direction (length of channels) may be between about 30 mm and about 150 mm, providing support for needles inserted through the grid to insertion depths usually encountered, e.g., in brachytherapy procedures.

In use, the channel block 102 is mounted relative to the grid 112 such that the distance between the grid 112 and the front face 220 of the channel block 102 is between about 0 mm and about 20 mm, to provide easy transition from the needle 108 travelling through the grid 112 and into the channels 104. The channel block 102 is mounted relative to the grid 112 such that the channels 104 are perpendicular to a grid plane. The mounting is achieved by attaching the channel block 102 to the grid template 112 directly or to the stepper 116 on which the grid 112 is mounted. A spacer or other offset device may be employed between the channel block 102 and the grid 112.

In other embodiments, the channel block 102 may be constructed of a multitude of slabs that are stacked together instead of being manufactured from a single piece of material. Stacking multiple, thinner slabs together greatly simplifies the manufacturing process since the creation of a very small-diameter for a relatively long channel is difficult. The channel block 102 may also feature one or a multitude of non-parallel channels. The channel block 102 may also feature channels that are curved instead of straight, to more closely resemble HDR catheter implantation patterns in actual patients. To verify tracking accuracy in curved channels, the system would work with either a flexible tracked needle or with a tracked guidewire with a tracking sensor at its tip. The needle or guidewire would need to be sufficiently flexible to permit travel through the curved channels.

The channel block 102 may include adjustable channel sizes and/or adjustable channel spacings. This may be implemented by having multiple sections of the channel block 102, which could be removed or adjusted relative to other portions of the channel block 102. The channel block 102 may also include a channel geometry customized for specific individual grid templates on the market, e.g. a grid template 112 with hole spacings other than 2.5 or 5 mm would call for a channel block 102 with the same non-standard channel spacing.

In one embodiment, the channel block 102 may be customized in size, shape, or in the distribution, shape or size of its channels 104 to closely resemble an expected or planned needle/catheter insertion pattern of a patient. This would permit establishing the system accuracy more precisely for a specific patient (or a specific group of patients with similar characteristics), instead of relying on a universal, non-patient-specific accuracy measure.

In one embodiment, the channel block 102 may be employed instead of the grid 112. The channel block 102 may be mounted on the stepper 116 (FIG. 1) instead of the grid 112 being mounted there or instead of the channel block 102 being mounted in some fixed position relative to the grid 112. In this way, the channel block 102 operates as the grid 112 to provide a location for the injection of needles 108 during a procedure. During calibration (QA/QC checks), the channel block 102 is employed as described above to calibrate or recalibrate the system 100.

Referring again to FIG. 1, the software module 126 runs on the workstation 118 as part of a QA system. The module 126 may perform the following tasks and features. The module 126, using the display 120 and a user interface 123, prompts and guides the user to follow a specific workflow for each QA experiment. The interface 123 may include a keyboard, mouse, a joystick, a haptic device, or any other peripheral or control to permit user feedback from and interaction with the workstation 118. This ensures that each QA experiment is performed in the same reproducible manner, and that the appropriate data is acquired and processed in each experiment. The module 126 acquires and stores needle tracking data from each insertion of the tracked needles 108 into the channels 104. Each data set may be referred to as a "needle track".

Once at least one needle track is acquired, the module 126 calculates the deviation of the measured track from an expected track, and compares the deviation with the accuracy requirements for the system 100. The calculation of the deviation depends on the geometry of the channels 104 in the channel block 102. For straight, parallel channels, e.g., the calculation involves determining the straight line that is the principle axis (main direction) of the needle track and quantifying a mean absolute deviation of the needle track from that line. The accuracy requirement could then be specified as the maximum deviation from a straight line that is tolerable. Once sufficient data is acquired, the module 126 determines if the system 100 meets requirements and provides this information to the user (in graphical, text-based, audible and/or other format) through the interface 123 or display 120.

If the system 100 does not meet requirements, the module 126 may prompt the user to acquire more needle tracks until sufficient data for tracking data correction is acquired. Tracking data correction can be performed with one or several methods. In one embodiment, the correction entails finding a correction function f: $(x,y,z) \rightarrow (x', y', z')$ that maps each point $(x,y,z)$ measured in the original tracking coordinate system onto corrected coordinates $(x', y', z')$. With the channel block 102 and system 100, tracking position data $(x,y,z)$ is measured inside the known geometry of the channels 104, which means that the true $(x', y')$ coordinates are always known for each z position, and the true $z'$ can be derived, e.g., from the physical insertion depth of the tracked needle into the channel block 102. With the aid of the channel block 102 and the rest of system 100, a set of measured 3D point pairs $[(x,y,z), (x',y',z')]$ can be obtained, and an interpolation function can be defined to obtain the correction function f for all points $(x,y,z)$, not just the measured points. The module 126 also maintains a log of each QA experiment and facilitates reviewing such logs to validate that a proper QA process has been followed.

Figure 3:
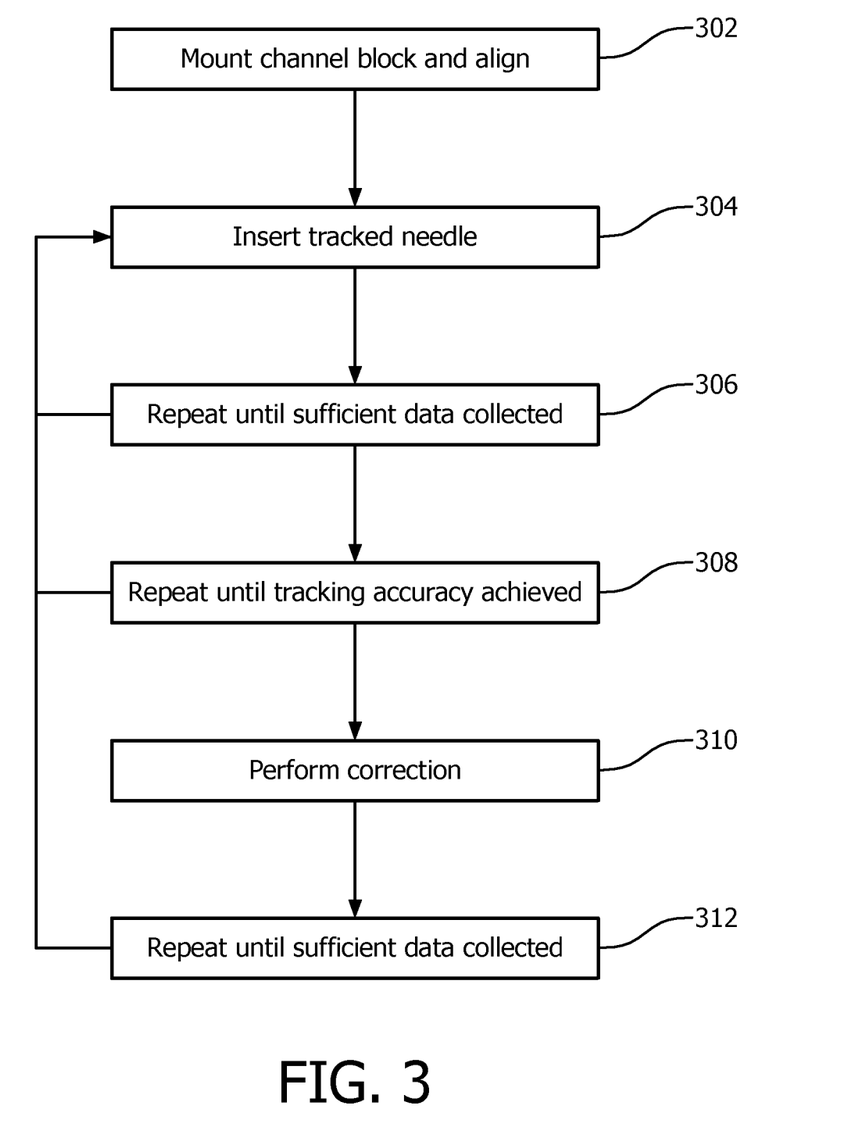
FIG. 3 is a block/flow diagram showing an illustrative workflow for calibrating the system of FIG. 1 in accordance with one embodiment.

Referring to FIG. 3, a block/flow diagram describes a workflow that may be followed for each QA experiment. In a particularly useful embodiment, a user is guided through the workflow with the aid of the software module 126 running on the workstation 118 of FIG. 1. In block 302, a channel block is mounted on a grid or stepper. Holes in the grid are aligned with channels formed in the channel block as described above. In block 304, a tracked needle is inserted through a grid hole into a channel in the channel block. After the insertion, the needle is refracted. In block 306, block 304 is repeated until sufficient data has been acquired to determine whether or not tracking accuracy is meeting requirements. In block 308, if the tracking accuracy does not meet requirements, further repeat block 304 until the software determines that sufficient data is acquired to correct for tracking inaccuracies. In block 310, carry out a correction in accordance with an analysis of the tracked data. In block 312, if such correction was carried out, repeat block 304 until sufficient data is acquired to verify that the corrected tracking data now meets requirements.

Figure 4:
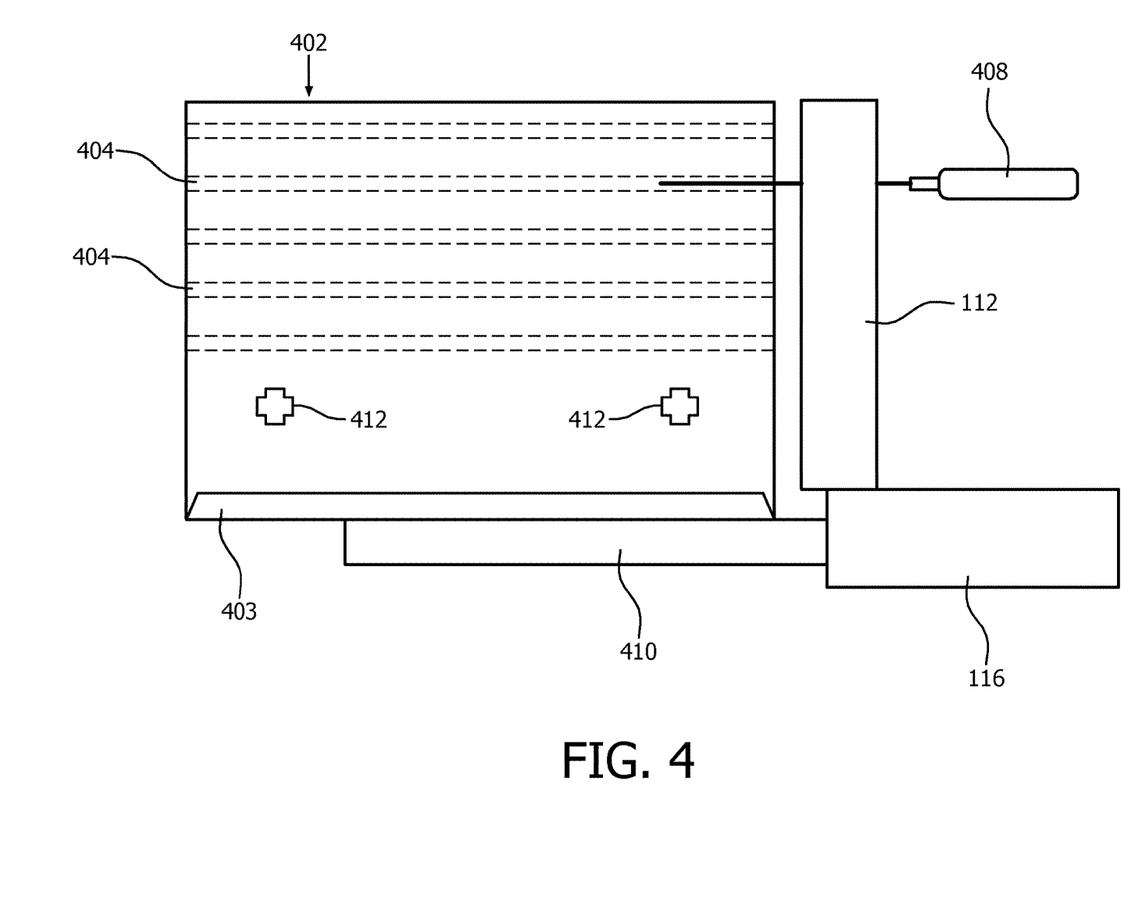
FIG. 4 is a side view showing a channel block configured to permit ultrasonic tracking capability for a position of an ultrasonic probe in accordance with one embodiment.

Referring to FIG. 4, a channel block 402 is illustratively depicted in accordance with another embodiment. The channel block 402 is configured to permit ultrasonic capability for tracking a position of an ultrasonic probe 410. This embodiment enables the position of the probe 410 to be checked against expected values to determine the accuracy of ultrasonic tracking data. The channel block 402 may be at least partially ultrasound-imaging compatible for the probe 410, which may be mounted on the stepper (116), and thus facilitate QA not only for the tracking of needles 408, but also QA for tracking of and imaging with the probe 410.

The channel block 402 includes an acoustic window 403 corresponding to a position of the probe 410 (e.g., a bottom of the channel block 402). The acoustic window 403 permits the transmittance of ultrasonic waves through channel block 402. In this regard, the channel block 402 has at least some material accessible through the acoustic window 410 that has approximately a same nominal speed of sound as that of tissue (e.g., approximately 1540 m/s). The channel block 402 may be formed entirely from a material that has approximately the same nominal speed of sound as that of tissue. The channel block 402 includes ultrasonically visible features with known geometry that can serve to assess a geometric accuracy or level of distortion of the ultrasound image. In particular, channels 404 may serve as such features, but they may be complemented by additional features 412 that may provide more convenient spatial comparisons. Examples of features that can be used for ultrasound QA include, e.g., wires in known locations, including wires parallel to the x-axis, y axis, and z-axis, that allow checking the accuracy of the 3D spatial representation in ultrasound; and an inclusion (e.g. ellipsoidal) with known volume and geometry, etc. In one embodiment, the ultrasound probe 410 may be employed for tracking ultrasonic sensors or materials provided in a needle(s) 408. In this way, the ultrasonic energy may be employed for QA/QC calibration.

In one example, the ultrasonic probe 410 may be tested for accuracy in much the same way as the needles 108 described above. For example, a position of the ultrasonic probe 410 can be employed to gather image data with known geometrical features (412) with expected positions/geometry. The image data can be compared with an ultrasonic image or a phantom taken or provided with the probe 410 having a correct orientation with the same known geometrical features (412) with expected positions/geometry. The program module 126 in this case can also suggest corrective actions to increase accuracy if the ultrasonic images differ. This may include adjusting one or several parameters on the ultrasonic system that affect the image geometry such that the image geometry matches the known geometry in the phantom or image.

Figure 5:
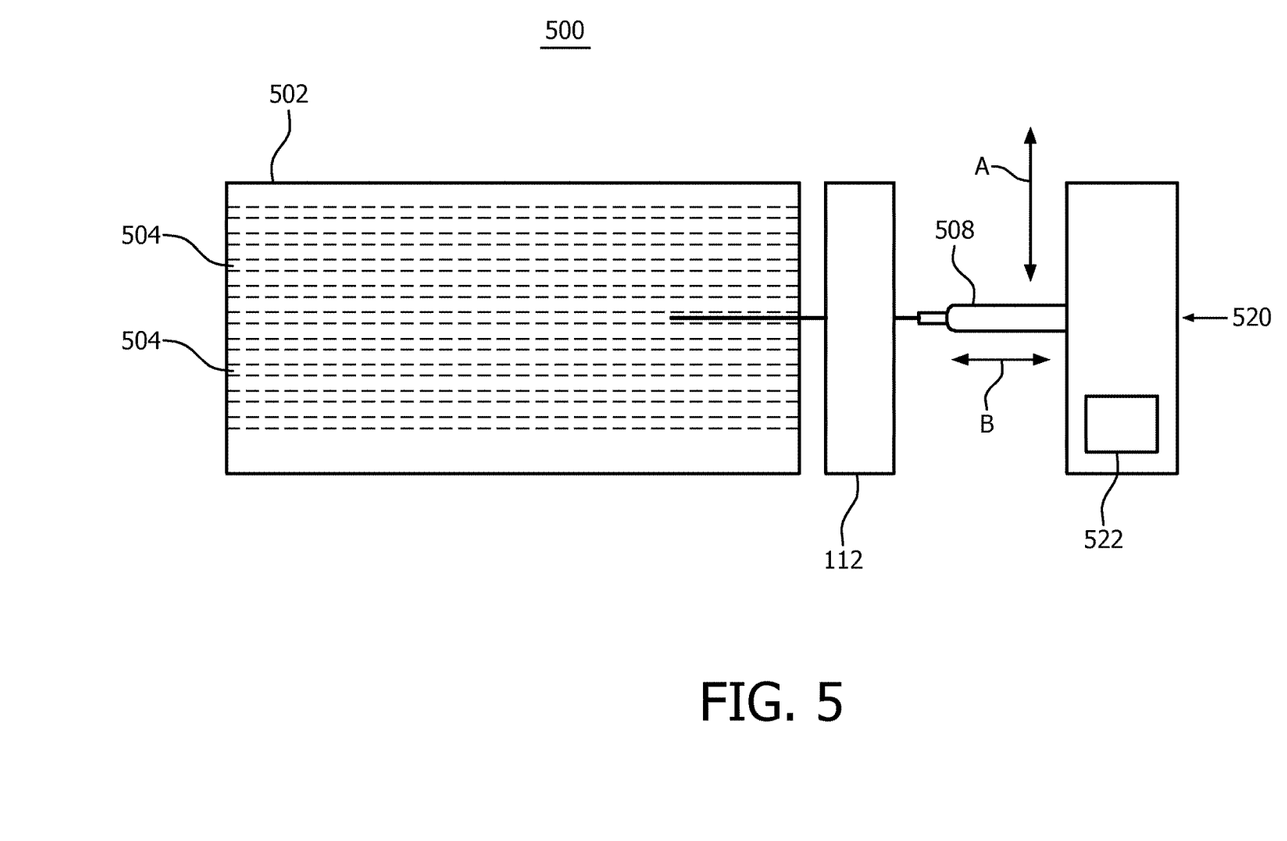
FIG. 5 is a side view showing a mechanism for automatically inserting and locating tracking needles or catheters in a channel block in accordance with one embodiment.

Referring to FIG. 5, in accordance with another embodiment, a system 500 includes a mechanism 520 to automatically insert a tracked needle or needles 508 and/or tracking sensor into a multitude of channels 504 of a channel block 502. A controller or control software 522 may be independently provided or may be part of the on the workstation 118 (FIG. 1). The controller 522 activates automatic needle insertion (instead of prompting the user for manual insertion) and can move needle 508 in the direction of arrows "A" and "B" and into or out of the page (three dimensions). The mechanism 520 may include a plurality of needles 508 corresponding to grid locations or a single needle may be repositioned and inserted automatically.

Figure 6:
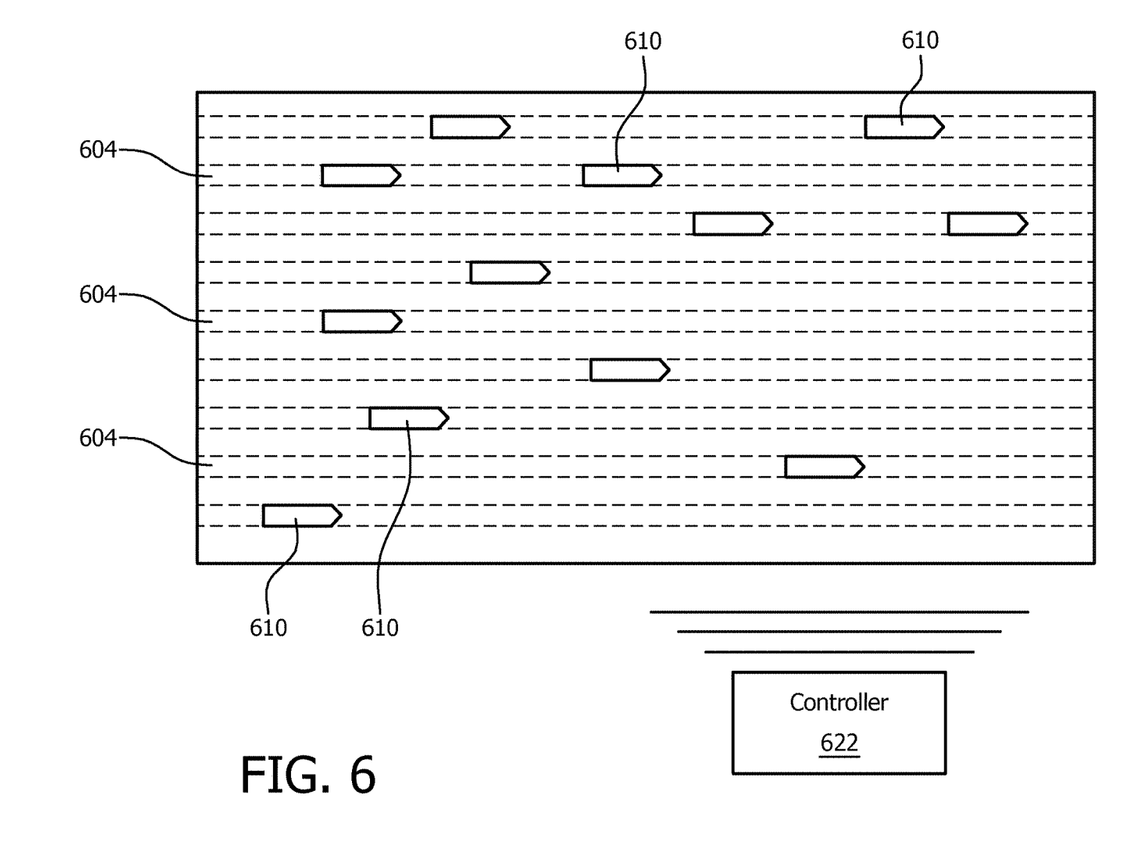
FIG. 6 is a perspective view of a channel block having a plurality of sensors pre-inserted at various depths in each of the channels to obtain tracking data from one or several of the sensors at a time in accordance with another embodiment.

Referring to FIG. 6, in accordance with another embodiment, a channel block 602 includes a plurality of sensors 610 pre-inserted at various depths in each of channels 604. A controller or control software 622 may be provided independently or may be part of the workstation 118 (FIG. 1). The controller or switch unit 622 (such as, e.g., a multiplexer) may be employed to obtain tracking data from one or several of the sensors 610 at a time. In this way, no manual or automatic insertion or motion of the needles would be needed. The controller 622 may communicate through wires or wirelessly. The sensors 610 may include EM sensors, ultrasound markers, etc. This embodiment is shown without the use of a grid (112).

Figure 7:
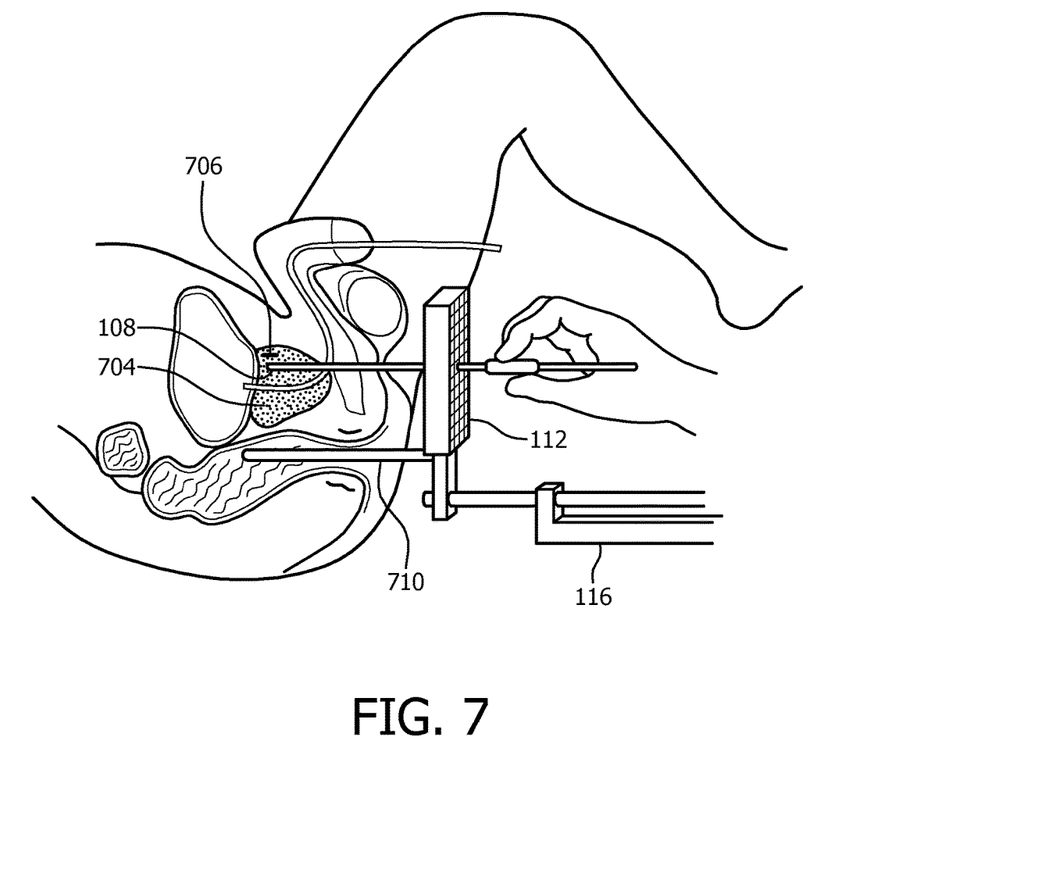
FIG. 7 is a side view of a brachytherapy system with transrectal ultrasonic (TRUS) guidance for trans-perineal LDR seed implantation with a subject shown in cross-section, the system being calibrated in accordance with the present principles.

Referring to FIG. 7, a brachytherapy setup is illustratively depicted in accordance with one embodiment. After the calibration using a QA/QC workflow, a procedure is employed which takes advantage of the highly reliable and accurate calibration of the system 100 as performed in accordance with the present principles. The grid 112 is employed to locate a trans-perineal needle 108 for insertion into a prostate 704. The needle 108 carries and injects radioactive seeds 706 in the prostate 704. The seeds 706 may include low-dose rate (LDR) brachytherapy seeds.

As described above, the grid 112 is mounted on the stepper 116 and a transrectal ultrasonic imaging probe 710 is employed to image the region. In LDR brachytherapy, radioactive seeds 706 are permanently implanted into the prostate 704 using the needle 108 to access to the prostate 704 through the grid 112, and with the aid of transrectal ultrasound (TRUS) image guidance (using probe 710). In HDR brachytherapy, catheters (108) are temporarily implanted into the prostate trans-perinealy and with TRUS guidance, followed by computer-controlled temporary insertion of a high-dose rate radioactive source into the catheters (108).

Figure 8:
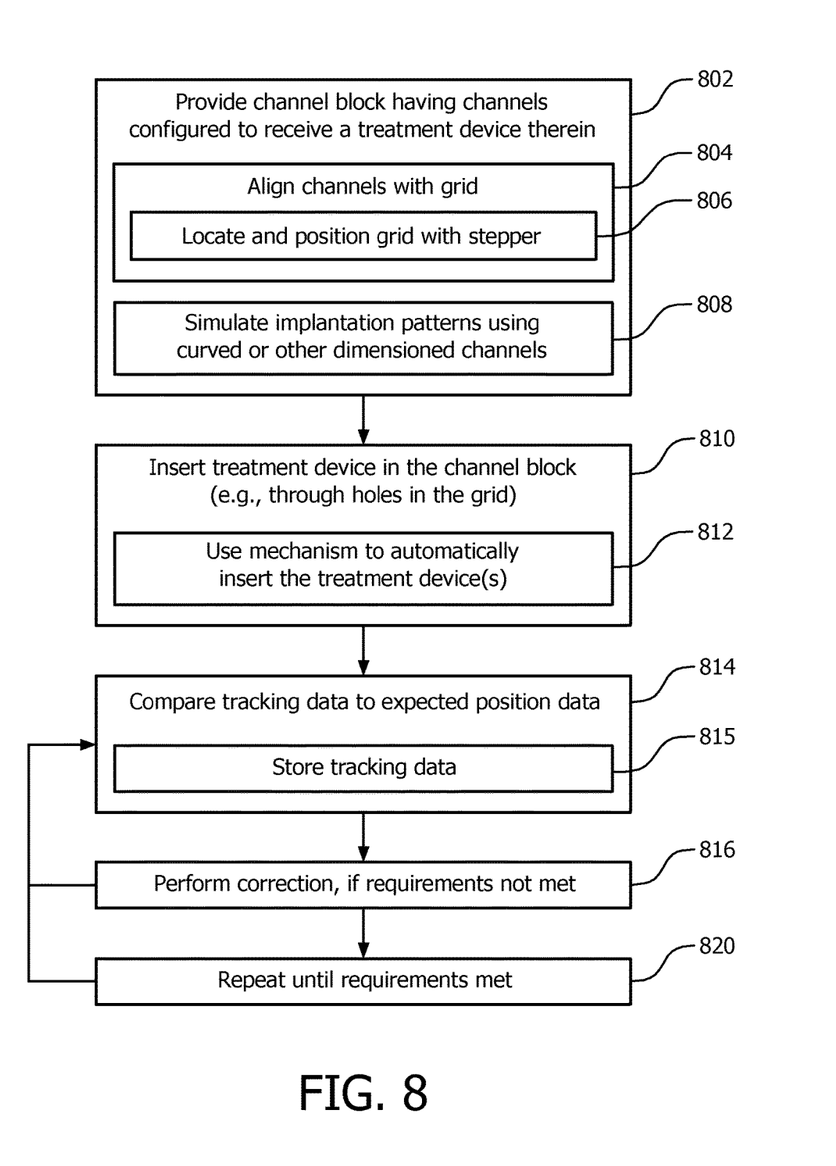
FIG. 8 is a block/flow diagram showing a method for calibrating and quality assurance for a medical procedure in accordance with the present principles.

Referring to FIG. 8, a method for calibration of a system for use with a medical procedure (e.g., brachytherapy) or for use as a training system is illustratively provided. In block 802, a channel block is provided. The channel block may include a plurality of different configurations, which may be customized in accordance with an application to be performed. The channel block has a plurality of channels formed therein. The plurality of channels is configured to correspond to locations where treatment devices are inserted for treatment of a patient or for training a technician for performing such a procedure. The channels are dimensioned to restrict motion of the treatment devices.

In block 804, the plurality of channels are preferably arranged to correspond with a grid employed for locating the treatment devices. The grid is aligned with or to corresponding channels of the channel block. In block 806, the aligning of the channels to the grid includes positioning and configuring the grid using a stepper.

In block 808, implantation patterns may be simulated by providing curved channels or channels having various dimensional features. The implantation patterns simulated by the channel block may correspond to anatomical features that could be encountered that are not easily navigated, such as, e.g., bones, vital organs etc.

In block 810, a position of at least one treatment device inserted in at least one of the channels of the plurality of channels is tracked using a tracking system configured to generate tracking data for the at least one treatment device. In block 812, the inserting may be performed by a robot or other mechanism which automatically located and inserts the treatment device or devices in the channels.

In block 814, the tracking data is compared with expected position data for the at least one treatment device. The tracking system may include an electromagnetic tracking system and the at least one treatment device may include an electromagnetic sensor, although other tracking systems may be employed. In block 815, electromagnetic or other tracking data is stored for comparing the tracking data with the expected position data. The expected data may be based on the channel locations, grid specifications, etc.

In block 816, a correction is performed or provided if comparing the tracking data with the expected position data does not meet requirements. In block 820, the comparison step of block 814 and/or the correction step of block 816 may be repeated until the requirements are met. The methods described may be employed for the measurement and correction of other systems, e.g., an imaging system, such an ultrasonic imaging system. In such a case, the channel block includes features employed in comparing and correcting the ultrasonic probe placement or ultrasonic imaging parameters. Blocks 810-820 may be employed to compare the ultrasonic probe's position and collected data for reference features in the channel block.

In interpreting the appended claims, it should be understood that:
   a) the word "comprising" does not exclude the presence of other elements or acts than those listed in a given claim;
   b) the word "a" or "an" preceding an element does not exclude the presence of a plurality of such elements;
   c) any reference signs in the claims do not limit their scope;
   d) several "means" may be represented by the same item or hardware or software implemented structure or function; and
   e) no specific sequence of acts is intended to be required unless specifically indicated.

Having described preferred embodiments for quality assurance for navigation-assisted procedures (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A calibration system for a tracking system, comprising:
a channel block having a plurality of channels formed therein, the plurality of channels being configured to correspond to locations where treatment devices are inserted for treatment of a patient, the channels being dimensioned to restrict motion of the treatment devices; and
the tracking system configured to monitor a position of at least one treatment device inserted in at least one of the channels of the plurality of channels, the tracking system being configured to generate tracking data for the at least one treatment device as the treatment devices move through the plurality of channels for comparison from within a corresponding channel with an expected position based on the true positional data for the at least one treatment device from within the corresponding channel, the expected path data include one or more of a particular grid position a stepper setting, arbitrarily set data, and data from a surgical plan.

2. The system as recited in claim 1, wherein the plurality of channels are arranged to correspond with a grid employed for locating the treatment devices.

3. The system as recited in claim 2, wherein the grid includes holes which are aligned with the plurality of channels such that the at least one treatment device is inserted in one of the channels by passing through one of the holes in the grid.

4. The system as recited in claim 2, further comprising a stepper for positioning and configuring one of the grid and the channel block.

5. The system as recited in claim 1, wherein the tracking system includes an electromagnetic tracking system that is remote from the channel block, and the at least one treatment device includes an electromagnetic sensor.

6. The system as recited in claim 1, wherein the at least one treatment device includes one of a needle and a catheter.

7. The system as recited in claim 1, wherein the channel block includes an acoustic window which permits transmittance of ultrasonic waves.

8. The system as recited in claim 1, wherein the channel block includes a material that simulates acoustic properties of living tissue.

9. The system as recited in claim 1, further comprising a workstation including a processor and memory, the memory storing a program module configured to collect the tracking data for comparison with expected position data for the at least one treatment device.

10. The system as recited in claim 9, wherein the program module is configured to provide workflow instructions for a user through an interface for quality assurance reporting, reviewing process steps, tracking data and archiving data.

11. The system as recited in claim 9, further comprising a warning mechanism configured to be responsive to a determination that the tracking data and the expected position data for the at least one treatment device do not meet requirements.

12. The system as recited in claim 1, wherein the channels include curved channels to simulate implantation patterns.

13. The system as recited in claim 1, further comprising a mechanism for automatically locating and inserting the at least one treatment device in the channels.

14. A method for calibration of a tracking system, comprising:
providing a channel block having a plurality of channels formed therein, the plurality of channels being configured to correspond to locations where treatment devices are inserted for treatment of a patient, the channels being dimensioned to restrict motion of the treatment devices;
tracking a position of at least one treatment device inserted in at least one of the channels of the plurality of channels using a tracking system configured to generate tracking data for the at least one treatment device as the treatment devices move through the plurality of channels; and
comparing the tracking data from within a corresponding channel with expected position data based on true positional data from within the corresponding channel for the at least one treatment device.

15. The method as recited in claim 14, further comprising performing a correction if comparing the tracking data with the expected position data does not meet requirements and repeating the comparing and performing steps until the requirements are met.

16. A calibration system, comprising:
a channel block having a plurality of channels formed therein, the plurality of channels being configured to correspond to locations where treatment devices are inserted for treatment of a patient, the channels being dimensioned to restrict motion of the treatment devices;
a tracking system configured to monitor a position of at least one treatment device inserted in at least one channel of the plurality of channels, the tracking system being configured to generate tracking data that tracks positions of the at least one treatment device; and
one or more processors programmed to:
receive the tracking data from the tracking system as the treatment devices move through the plurality of channels;
determine a current position of the at least one treatment device from within a corresponding channel; and
compare the current position determined from the received tracking data with an expected position of the at least one treatment device from within the corresponding channel.

17. The system as recited in claim 16, wherein the plurality of channels are arranged to correspond with a grid having holes aligned with the plurality of channels such that the at least one treatment device is inserted in one of the channels by passing through one of the holes in the grid.

18. The system as recited in claim 16, wherein the tracking system includes an electromagnetic tracking system that is remote from the channel block, and the at least one treatment device includes an electromagnetic sensor.

19. The system as recited in claim 16, further comprising a robotic device configured to automatically locate and insert the at least one treatment device in the channels.

20. The system as recited in claim 16, further comprising:
a warning mechanism configured to issue a warning responsive to the current position from the tracking data and the expected position for the at least one treatment device differing by more than a preselected degree.

* * * * *